United States Patent
Wambier et al.

(10) Patent No.: US 11,576,812 B2
(45) Date of Patent: Feb. 14, 2023

(54) METHODS FOR REDUCING BODY FAT IN A SUBJECT

(71) Applicants: Carlos Wambier, Hamden, CT (US); John E. Kulesza, Wethersfield, CT (US); Doris Hexsel, Porto Alegre (BR)

(72) Inventors: Carlos Wambier, Hamden, CT (US); John E. Kulesza, Wethersfield, CT (US); Doris Hexsel, Porto Alegre (BR)

( * ) Notice: Subject to any disclaimer, the term of this patent is extended or adjusted under 35 U.S.C. 154(b) by 291 days.

(21) Appl. No.: 16/857,814

(22) Filed: Apr. 24, 2020

(65) Prior Publication Data

US 2020/0337891 A1 Oct. 29, 2020

Related U.S. Application Data

(60) Provisional application No. 62/838,566, filed on Apr. 25, 2019.

(51) Int. Cl.
*A61F 7/00* (2006.01)

(52) U.S. Cl.
CPC .... *A61F 7/0085* (2013.01); *A61F 2007/0063* (2013.01); *A61F 2007/0087* (2013.01)

(58) Field of Classification Search
CPC ............. A61B 18/02; A61B 2018/0293; A61F 2007/0003; A61F 2007/0014; A61F 2007/0022; A61F 2007/0023; A61F 2007/0031; A61F 2007/0041; A61F 2007/0063; A61F 2007/0087; A61F 2007/029; A61F 2007/126; A61F 7/0085; A61F 7/12
See application file for complete search history.

(56) References Cited

U.S. PATENT DOCUMENTS

| | | | |
|---|---|---|---|
| 2003/0220674 A1* | 11/2003 | Anderson | A61B 5/6804 607/104 |
| 2012/0197361 A1* | 8/2012 | Gonzales | A61F 7/12 607/105 |
| 2017/0274011 A1 | 9/2017 | Garibyan et al. | |
| 2019/0000663 A1 | 1/2019 | Anderson et al. | |

OTHER PUBLICATIONS

Garibyan, L. et al., Subcutaneous Fat Reduction with Injected Ice Slurry, Downloaded Jan. 20, 2020 from https://journals.lww.com/plasreconsurg.

* cited by examiner

*Primary Examiner* — Tigist S Demie

(74) *Attorney, Agent, or Firm* — Dinsmore & Shohl LLP; Weston R. Gould

(57) ABSTRACT

Methods are provided for reducing body fat, volume of fat pads, and/or lipoma(s) in a subject. The methods as provided herein may include injecting a fat-sculpting liquid into a treatment region of the subject, wherein the fat-sculpting liquid has a temperature of −25° C. to 10° C. when injected and is substantially free of frozen particulates. The methods for reducing body fat in a subject may further include injecting a fat-sculpting liquid comprising saline and benzyl alcohol into a treatment region of the subject, wherein the fat-sculpting liquid has a temperature of −15° C. to 5° C. when injected and is substantially free of frozen particulates.

26 Claims, No Drawings

METHODS FOR REDUCING BODY FAT IN A SUBJECT

CROSS-REFERENCE TO RELATED APPLICATION

This application claims priority to U.S. Application No. 62/838,566, filed Apr. 25, 2019, the entire contents of which are incorporated in their entirety.

FIELD

The present disclosure generally relates to methods for reducing body fat in a subject. More specifically, methods are provided that locally disrupt lipid-rich adipose cells by the injection of a fat-sculpting liquid at controlled temperatures, with the objective of reducing the volume of targeted fat pads or fat-tissue benign tumors (lipomas).

BACKGROUND

The subcutaneous fatty tissue of newborn children is acutely sensitive to cold temperatures. In newborns, the intracellular lipid content of the subcutaneous fat cells, or adipocytes, includes increased ratios of saturated triglycerides. As newborn children mature, the ratio of saturated to unsaturated fatty acids among intracellular triglycerides of adipocytes gradually decreases, which leads to increased amounts of unsaturated fatty acids during the maturation process. Having a higher content of unsaturated fatty acids correlates with more protection against cold temperatures, thereby gradually decreasing the occurrence of cold panniculitis. Cold panniculitis is a natural phenomenon that occurs when a fat pad is directly exposed to freezing temperatures, causing adipocyte cell necrosis due to crystallization of adipocyte triglycerides. Cold panniculitis results in lipoatrophy of the affected fat pads.

In adults, the intracellular lipid content varies among cell types. Dermal and epidermal cells, for instance, have relatively low unsaturated fatty acid concentrations compared to the underlying adipocytes, which form the subcutaneous fatty tissue. Many adults are dissatisfied with the amount of subcutaneous fatty tissue present in their bodies. It would therefore be highly desirable to reduce the volume of fat-pads with precision, through minimally invasive procedures that directly target adipocytes of the subcutaneous fat tissue without causing injury to the surrounding dermal and epidermal tissue. While health and cosmetic benefits are known to result from reduction of fatty tissue, current invasive, minimally invasive, or non-invasive fat-reduction methods involve a variety of health risks, inconsistent results, and return visits that are time consuming and costly.

Current methods for invasive removal of subcutaneous fatty tissue include removing fat from the subject's body via surgery, through a skin incision that leave long linear scars, or by means of a cannula attached to an aspirator (i.e., different methods of liposuction). However, liposuction is considered to be a major surgical procedure, which is associated with a variety of risks. Kaoutzanis et al., *Cosmetic Liposuction: Preoperative Risk Factors, Major Complication Rates, and Safety of Combined Procedures, Aesthetic Surgery Journal* 37(6): 680-94 (2017). These risks may include, but are not limited to, scars, contour irregularities, fluid accumulation, numbness, infection, perforation of an internal organ, fat embolism, organ failure, livedo reticularis, or hematoma/lidocaine toxicity. Dixit et al., *Unfavorable outcomes of liposuction and their management, Indian Journal of Plastic Surgery* 46 (2): 377-92 (2013). Further, research has shown that liposuction has only minimal effects on long-term weight loss as the procedure does not address many of the underlying problems related to obesity. Hernandez et al., *Fat Redistribution Following Suction Lipectomy: Defense of Body Fat and Patterns of Restoration, Obesity Journal* 19(7): 1388-95 (2011).

Current methods for non-invasive removal of subcutaneous fatty tissue include selective disruption of fatty tissue by controlled cooling (i.e., cryolipolysis). U.S. Pat. No. 8,840,608 describes systems and methods for the selective disruption of lipid rich cells in a non-infant human subject by applying a thermoelectric cooling element to the subject's epidermal tissue. However, the risks associated with the systems and methods described may include skin burns, atrophy, cutaneous nerve terminal damage, and paradoxical adipose hyperplasia. Jalian et al., *Paradoxical Adipose Hyperplasia After Cryohpolysis, The Journal of the American Medical Association Dermatology* 150(3): 317-19 (2014).

Additionally, the cryolipolysis systems and methods are costly and require time intensive procedures that last for an hour or longer and/or require the subject to return for a number of consecutive procedures over the course of months or even years in order to achieve their desired results. Moreover, cryolipolysis systems may only execute the procedure if they adjust to the specific area to create suction. Some patients cannot perform such procedure in one side of the body because of the body surface convexity (i.e., one individual with bilateral pseudo gynecomastia, fat pads in the breasts, may perform cryolipolysis in a single side because the device did not attach to the other side). Therefore, multiple applicator/handpieces shapes are required to adjust to different body contours and fat pad size, which is also costly.

Methods of cryolipolysis include local treatment with injectable slurries comprising sterile ice particles. U.S. Pat. Pub. No. 2017/0274011 describes methods of subcutaneous injection of a cryoslurry in order to locally reduce subcutaneous fat. However, injection of ice crystal-containing slurries requires large diameter needles or catheters in order to avoid clogging delivery systems and may present additional challenges to the patient, such as pain, bruising, and scarring at the treatment site. Further, slurries comprising ice crystals are unstable solutions and may require special care to manufacture, store, and administer.

Current methods for minimally invasive removal of subcutaneous fatty tissue include chemical disruption of fatty tissue by injection of a surfactant. Deoxycholic acid is a bile acid which emulsifies and solubilizes dietary fats in the intestine, and when injected subcutaneously, it disrupts cell membranes in adipocytes and destroys fat cells in that tissue (see, e.g., U.S. Pat. Nos. 7,622,130 and 8,367,649), or the injection of medicinal corticosteroids to cause fat atrophy (e.g., U.S. Pat. No. 9,408,857). Deoxycholic acid may cause intense pain, dermal and epidermal necrosis if the injection is superficial, and corticosteroids may cause dermal and epidermal atrophy if the injection is superficial. Both techniques may only be applied at minimal amounts per treatment because the treatments are based on chemical/pharmacologic properties, systemic absorption at increased volumes is a great limitation of those techniques.

Further methods for minimally invasive removal of subcutaneous fatty tissue include cosmetic lipoatrophy, such as the methods described in U.S. Pat. No. 10,213,441. These methods allow for the nonsurgical removal of subcutaneous accumulations of fat of the face and beyond with a subcutaneous administration of Triamcinolone or other corticosteroids. However, such methods are focused exclusively to small areas of tissue. The method also may be further associated with the negative systematic side effects of long-term steroid exposure as well as the risk of skin discoloration and/or skin atrophy.

Therefore, there exists a need for methods for locally disrupting lipid-rich adipose cells so as to reduce the volume of fat pads and/or lipomas present in a subject.

SUMMARY

The following summary is provided to facilitate an understanding of some of the innovative features unique to the present disclosure and is not intended to be a full description. A full appreciation of the various aspects of the disclosure can be gained by taking the entire specification, claims, drawings, and abstract as a whole.

The methods provided herein reduce the risks associated with currently-known invasive and non-invasive removal of subcutaneous fatty tissue such as pain, skin burns, scars, atrophy, cutaneous nerve terminal damage, paradoxical adipose hyperplasia, contour irregularities, fluid accumulation, infection, internal puncture of an organ, fat embolism, organ failure, or lidocaine toxicity, and post-inflammatory hyperpigmentation.

Accordingly, methods of reducing body fat in a subject are provided herein. In one aspect, the methods include injecting a fat-sculpting liquid into a treatment region of the subject, optionally injecting into the adipose tissue of the subject, wherein the fat-sculpting liquid has a temperature of negative 25 degrees Celsius (−25° C.) to ten degrees Celsius (10° C.) when injected, optionally wherein the fat-sculpting solution is substantially free of frozen particulates.

In other aspects, the methods include injecting a fat-sculpting liquid comprising saline and benzyl alcohol into a treatment region of the subject, wherein the fat-sculpting liquid has a temperature of negative fifteen degrees Celsius (−15° C.) to five degrees Celsius (5° C.) when injected, optionally wherein the fat-sculpting solution is substantially free of frozen particulates.

These and other objects, features, aspects, and advantages will become apparent to those of ordinary skill in the art from a reading of the following detailed description and the appended claims.

DETAILED DESCRIPTION

Provided herein are methods having utility for reducing body fat in a subject. The method includes injecting a fat-sculpting liquid into a treatment region of the subject, wherein the fat-sculpting liquid has a temperature of −25° C. to 10° C. when injected. Without being bound by theory, the injections are believed to locally disrupt lipid-rich adipose cells by rapidly decreasing their temperature, which make the injections suitable for reducing the overall volume of fat pads present in the subject. In aspects, the fat-sculpting solution is substantially free of frozen particulates.

Optionally, lipid-rich cells described in the present disclosure are adipocytes within subcutaneous fatty tissue or surrounding cellulites. Thus, lipid-rich cells that include the subcutaneous adipose tissue are precisely targeted for disruption by methods described herein.

In aspects, fat-sculpting liquid is injected into a treatment region of a subject. A "treatment region," as used herein, refers to a region of the subject's body in proximity to adipose tissue or other lipid-rich tissue. The treatment region may include any suitable body part or extremity of the subject. For example, treatment regions may include the chin below the jawline, the face, the arm, the flank, the abdomen, the inner thigh, the outer thigh, the distal thigh, the upper or lower leg, underneath the buttocks, the waist, and so forth, of a subject. Optionally, the fat-sculpting liquid is injected into body parts or extremities that have excessive amounts of lipid-rich (i.e., fatty) cells that are targeted for elimination.

In aspects, fat sculpting liquid is injected into or proximate to a lipoma, or benign overgrowth of fat cells between the skin and underlying muscle. Lipomas are commonly found in the neck, shoulders, back, abdomen, arms, and/or thighs of a subject.

Optionally, lipid-rich cells targeted in the present disclosure are adipocytes located within subcutaneous fatty tissue or cellulite. Without being bound by theory, it is believed that selective disruption of lipid-rich cells by the processes as provided herein results from localized crystallization of highly saturated fatty acids upon the injection of the fat-sculpting liquid at controlled temperatures that do not induce crystallization of highly saturated fatty acids in non-lipid-rich cells. The crystals rupture the bilayer membrane of lipid-rich cells, thereby causing necrosis. Thus, damage or necrosis of non-lipid-rich cells, such as dermal cells, is avoided at temperatures of the fat-sculpting liquid that induce crystal formation in lipid-rich cells. It is also believed that injection of the fat-sculpting liquid induces metabolism of lipids of lipid-rich cells, further enhancing the reduction in subcutaneous adipose tissue.

In some embodiments, the fat-sculpting liquid includes saline or water. As used herein, the term "saline" means a sterile, nonpyrogenic, isotonic solution having an amount of sodium chloride and water with a pH from 4.5 to 7.0. As used herein, the term "water" means a sterile, nonpyrogenic, isotonic solution having water with a pH from 4.5 to 7.0. One or more freeze inhibitors is optionally supplemented into the saline or water, optionally with one or more other components, so as to form a fat-sculpting liquid as provided herein. Without being bound by theory, it is believed that the freeze inhibitor present in the in the saline and/or water functions to reduce the freezing temperature of the fat-sculpting liquid and may also serve as an antimicrobial agent, and/or an anesthetic.

Without being bound by theory, it is believed that injection of the fat-sculpting liquid at the temperature ranges as provided herein are suitable for locally disrupting lipid-rich cells while sparing the dermal tissue and/or epidermal tissue from unnecessary freezing and disruption. Moreover, it is believed that the injections of the fat-sculpting liquid at the temperature ranges as provided herein are suitable for crystallizing adipocyte fat and/or enhancing fat reduction in the subject.

Due to the freezing inhibition properties, the fat-sculpting liquid as provided herein, in some embodiments, is substantially free from frozen particulates. Solid particulates that may be excluded from the fat-sculpting liquid include, but are not limited to, ice particles. As such, in some embodiments, the fat-sculpting liquid comprises less than 0.1 percent by weight (wt. %) of ice particles, based on the total weight of the fat-sculpting liquid. In other embodiments, the fat-sculpting liquid comprises less than 0.05 wt. %, less than 0.01 wt. %, less than 0.005 wt. %, less than 0.001 wt. %, less than 0.0005 wt. %, or less than 0.0001 wt. % of ice particles, based on the total weight of the fat-sculpting liquid.

Fat-sculpting liquids free or substantially free of frozen particulates, including ice crystals, advantageously may be administered using any internal diameter needle or cannula, without concern for clogging of the needle or cannula with frozen particles. The fat-sculpting liquids described herein may be administered via fine needles or cannulas for precise, targeted delivery of a fat-sculpting liquid to a treatment region, while minimizing risk of pain, scarring, and/or bruising to the subject. Suitable needle gauges include, for example, from about 0.15 mm to about 2.0 mm in diameter, or any value or range therebetween. For example, needles of standard gauge of 14-40 may be used.

In embodiments, the fat-sculpting liquid may include one or more freeze inhibitors. Optionally, a fat-sculpting liquid includes benzyl alcohol in addition to one or more additional freeze inhibitors. Suitable freeze inhibitors may include glucose, sodium lactate, sodium chloride, potassium chloride, calcium chloride, benzyl alcohol, glycerin, ascorbic acid, or combinations thereof. The freeze inhibitor inhibits formation of frozen particulates in the injectable solution.

In some embodiments, the freeze inhibitor may also function as an additional antimicrobial agent and/or an anesthetic. Without being bound by theory, it is believed that the inclusion of the freeze inhibitor further reduces the freezing temperature of the fat-sculpting liquid, thereby allowing for a larger range of suitable injection temperatures and liquid injection into the target site so as to more effectively disrupt adipose tissue cells.

An anti-inflammatory agent, when used, may be added to the fat-sculpting liquid to minimize the inflammation caused by injection of the fat-sculpting liquid. Suitable anti-inflammatory agents may include, but are not limited to, synthetic corticosteroids, such as triamcinolone, methylprednisolone. The amount of anti-inflammatory agent may be effectively chosen to reduce or eliminate inflammation caused by the fat-sculpting liquid, the injection itself, or combinations thereof. Choice of the amount of anti-inflammatory agent and identify of the agent can be determined by one of ordinary skill in the art.

Further embodiments of the fat-sculpting liquid may include an anesthetic solution to induce a subject's insensitivity to pain caused by injection of the fat-sculpting liquid. Suitable anesthetic solutions may include, but are not limited to, any general anesthetics, local anesthetics, or even analgesics capable of producing a state of anesthesia within the subject for a limited duration of time. Examples of anesthetic solutions may include mepivacaine, bupivacaine, ropivacaine, chloroprocaine, procaine, articaine, epinephrine, lidocaine, and combinations thereof. In some embodiments, the anesthetic solution is present in the fat-sculpting liquid at concentrations from 0 wt. % to 2 wt. %, based on the total weight of the fat-sculpting liquid.

In embodiments, the fat-sculpting liquid may be co-administered with one or more vasoconstrictors such as epinephrine or norepinephrine, to reduce the chances of hematoma development and to provide longer periods of low temperature in the fat tissue such as by reducing the local blood flow.

In embodiments, the fat-sculpting liquid may further comprise one or more lipolytic agents to enhance reduction of lipid-rich cells. Exemplary lipolytic agents include biocompatible surfactants, bile salts and their derivatives (e.g., deoxycholic acid), phosphatidylcholine (lecithin), catecholamines, beta-2 adrenergic receptor agonists (e.g., isoproterenol), alpha-2 adrenergic receptor agonists (e.g., yohimbine), phosphodiesterase inhibitors (e.g., aminophylline, theophylline), corticosteroids, caffeine, hyalorunidase, collagenase, alpha-tocopherol, ethanol, benzyl alcohol, carnitine, catechin, cysteine, gallic acid, laminarin, rutin, myrecetin, alpha melanocyte stimulating hormone (alpha MSH), melilotus, resveratrol, genistein, and the like.

In some embodiments, the fat-sculpting liquid at administration has a temperature of −25° C. to 10° C., which includes all subranges therebetween, when injected into the subject. Other suitable injection temperatures of the fat-sculpting liquid, according to other embodiments, are from −25° C. to 8° C., from −25° C. to 6, from −25° C. to 5° C., from −25° C. to 4° C., from −25° C. to 2° C., from −25° C. to 0° C., from −25° C. to −2° C., from −25° C. to −4° C., from −25° C. to −5° C., from −20° C. to 10° C., from −20° C. to 8° C., from −20° C. to 6° C., from −20° C. to 5° C., from −20° C. to 4° C., from −20° C. to 2° C., from −20° C. to 0° C., from −20° C. to −2° C., from −20° C. to −4° C., from −20° C. to −5° C., from −15° C. to 10° C., from −15° C. to 8° C., from −15° C. to 6° C., from −15° C. to 4° C., from −15° C. to 2° C., from −15° C. to 0° C., from −15° C. to −2° C., from −15° C. to −4° C., or from −15° C. to −5° C. The fat-sculpting liquid may be cooled to these temperatures before it is introduced to an injection device or after it has been introduced to the injection device.

In embodiments, the injection of the fat-sculpting liquid preserves the dermal tissue temperature of the subject. As used herein, the term "preserves" means that the dermal tissue temperature is not reduced to the same low temperature of the subcutaneous injection site optionally, the dermal tissue temperature of the subject is not changed by greater than or equal to 10° C. Without being bound by theory, it is again believed that preserving the dermal tissue temperature will spare the dermal tissue and/or epidermal tissue from unnecessary freezing and disruption while still achieving the selective freezing and disruption of lipid-rich cells.

The injection of the fat-sculpting liquid may be achieved through any apparatuses suitable for injecting the fat-sculpting liquid directly into adipose tissue of the subject, thereby bypassing any contact between the fat-sculpting liquid and the dermal and/or epidermal layers of skin. Suitable apparatuses may include, but are not limited to, a syringe having any suitable volume and a needle. Optionally, the syringe is provided without silicone oil as a lubricant, which could escape during injections, resulting in granulomatous reactions and permanent filler effects. Optionally, the syringe is filled with an amount of the fat-sculpting liquid, packaged for distribution, and cooled before it is used to inject the subject with the fat-sculpting liquid.

Additional suitable injection devices include cannulas, catheters, tubing and/or pumps, and the like. Optionally, a control device may be used to control flow rate and volume of the fat-sculpting liquid delivered to a treatment region.

As such, the fat-sculpting liquid may be cooled before it is introduced to the syringe or after it has been introduced to the syringe by any suitable means capable of producing temperatures in the previously described ranges. Suitable means for cooling the fat-sculpting liquid and/or the syringe may include, but are not limited to, refrigerators freezers, ice, liquid nitrogen, cooled gels, salinized water, or combinations thereof.

The syringe may also be outfitted with a temperature monitor that signals upon the fat-sculpting liquid reaching a suitable temperature, which is previously described. Suitable temperature monitors may include, but are not limited to, LCD color thermal indicators, infrared non-contact thermometers, and/or a digital thermometer placed in or around the needle of the syringe. Without being bound by theory, it is believed that the signal provided by the temperature monitor ensures that the subject will not receive one or more unnecessary and painful injections of the fat-sculpting liquid, which has been cooled to suitable temperatures able to provide the desired results.

In embodiments, each injection administers 0.1 mL to 3.0 mL, or any other range or subrange therebetween, of the fat-sculpting liquid per square centimeter of adipose tissue. In other embodiments, each injection administers 0.2 mL to 2.5 mL, 0.3 mL to 2.0 mL, 0.4 mL to 1.5 mL, or 0.5 mL to 1.0 mL of the fat-sculpting liquid per square centimeter of adipose tissue. Without being bound by theory, it is believed that injection volumes outside of these ranges may be ineffective or require more punctures when too small volume boluses are injected or may cause overcorrection or irregular contour if large volumes are injected.

In some embodiments, the maximum amount of the fat-sculpting liquid injected into a subject is 30 mL per 24 hour period. Larger volumes may cause systemic hypothermia or systemic side effects of the absorption of the freezing inhibitors injected. In further embodiments, the maximum amount of fat-sculpting liquid injected into a subject is 3.0 mL per square centimeter of adipose tissue per 24 hour period.

Further methods of reducing body fat in a subject may include injecting a fat-sculpting liquid comprising saline and benzyl alcohol into the subject, wherein the fat-sculpting liquid has a temperature of −15° C. to 5° C. when injected. Such a method may incorporate any of the embodiments previously described within the present disclosure.

In some embodiments, a mild heat may be applied to the skin following injection of a fat-sculpting liquid to improve skin responses to the underlying injection. Heating may be in the form of a heating pad, infrared energy, gentle contact with another body part such as a hand, or other method. Heat may be applied for any desired time, but optionally for 10 seconds to 10 minutes or any value or range therebetween.

In some aspects, an imaging technique such as ultrasound, magnetic resonance, x-ray, and the like may be used to verify proper positioning of an injection device. In a specific embodiment, ultrasound may be used to guide injection and/or monitor administration of a fat-sculpting liquid as described herein.

The foregoing description of particular aspect(s) is merely exemplary in nature and is in no way intended to limit the scope of the disclosure, its application, or uses, which may, of course, vary. The disclosure is presented with relation to the non-limiting definitions and terminology included herein. These definitions and terminology are not designed to function as a limitation on the scope or practice of the disclosure but are presented for illustrative and descriptive purposes only. While the processes and devices are described as an order of individual steps or using specific arrangements of elements, it is appreciated that described steps or elements may be interchangeable such that the description includes multiple parts or steps arranged in many ways as is readily appreciated by one of skill in the art.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

It should be understood that every maximum numerical limitation given throughout the present disclosure includes every lower numerical limitation, as if such lower numerical limitations were expressly written herein. Moreover, every minimum numerical limitation given throughout the present disclosure will include every higher numerical limitation, as if such higher numerical limitations were expressly written herein. Finally, every numerical range given throughout the present disclosure will include every narrower numerical range that falls within such broader numerical range, as if such narrower numerical ranges were all expressly written herein.

Patents, publications, and applications mentioned in the specification are indicative of the levels of those skilled in the art to which the invention pertains. These patents, publications, and applications are incorporated herein by reference to the same extent as if each individual patent, publication, or application was specifically and individually incorporated herein by reference.

A number of embodiments of the invention have been described. Nevertheless, it will be understood that various modifications may be made without departing from the spirit and scope of the disclosure. Accordingly, other embodiments are within the scope of the following claims.

The invention claimed is:

1. A method of reducing body fat in a subject, the method comprising:
   injecting a fat-sculpting liquid into a treatment region of the subject, said fat-sculpting liquid comprising a freeze inhibitor comprising benzyl alcohol, wherein the fat-sculpting liquid has a temperature of −25° C. to 10° C. when injected and wherein the fat-sculpting liquid is substantially free of frozen particulates.

2. The method of claim 1, wherein the fat-sculpting liquid comprises less than 0.01 wt. % of frozen particulates, based on total weight of the fat-sculpting liquid.

3. The method of claim 1, wherein the fat-sculpting liquid comprises saline or water.

4. The method of claim 1, wherein the fat-sculpting liquid further comprises an anti-inflammatory agent, an anesthetic solution, or combinations thereof.

5. The method of claim 4, wherein the freeze inhibitor further comprises glucose, sodium lactate, sodium chloride, potassium chloride, calcium chloride, benzyl alcohol, glycerin, ascorbic acid, or combinations thereof.

6. The method of claim 1, wherein the injection is provided by a syringe.

7. The method of claim 1, wherein the fat-sculpting liquid is injected directly into adipose tissue of the subject.

8. The method of claim 1, wherein the injection crystallizes adipocyte fat, promotes cold panniculitis, enhances fat reduction, or combinations thereof.

9. The method of claim 1, wherein the fat-sculpting liquid has a temperature of −15° C. to 5° C. when injected.

10. The method of claim 1, wherein each injection administers 0.1 mL to 3.0 mL of the fat-sculpting liquid.

11. The method of claim 1, wherein each injection administers 0.5 mL to 1.0 mL of the fat-sculpting liquid.

12. The method of claim 1, wherein a maximum amount of the fat-sculpting liquid injected into the subject is 30 mL per 24 hour period.

13. The method of claim 1, wherein the injection of the fat-sculpting liquid preserves an epidermis and a dermal tissue temperature of the subject.

14. The method of claim 1, wherein the method reduces a risk of dermal fibroblast necrosis compared to traditional surface cryolipolysis techniques.

15. The method of claim 1, wherein the method reduces a risk of post-inflammatory hyperpigmentation compared to traditional surface cryolipolysis techniques.

16. A method of reducing body fat in a subject, the method comprising:

injecting a fat-sculpting liquid comprising saline and a freeze inhibitor comprising benzyl alcohol into a treatment region of the subject, wherein the fat-sculpting liquid has a temperature of −15° C. to 5° C. when injected and wherein the fat-sculpting liquid is substantially free of frozen particulates.

17. The method of claim 16, wherein the fat-sculpting liquid comprises less than 0.01 wt. % of frozen particulates, based on total weight of the fat-sculpting liquid.

18. The method of claim 16, wherein each injection administers 0.5 mL to 1.0 mL of the fat-sculpting liquid.

19. The method of claim 16, wherein the injection is provided by a syringe.

20. The method of claim 16, wherein a maximum amount of fat-sculpting liquid injected into the subject is 30 mL per 24 hour period.

21. The method of claim 16, wherein the fat-sculpting liquid is injected directly into adipose tissue of the subject.

22. The method of claim 16, wherein the injection crystallizes adipocyte fat, promotes cold panniculitis, enhances fat reduction, or combinations thereof.

23. The method of claim 16, wherein a maximum amount of the fat-sculpting liquid injected into the subject is 30 mL per 24 hour period.

24. The method of claim 16, wherein the injection of the fat-sculpting liquid preserves a dermal tissue temperature of the subject.

25. The method of claim 16, wherein the method reduces a risk of dermal fibroblast necrosis compared to traditional surface cryolipolysis techniques.

26. The method of claim 16, wherein the method reduces a risk of burns and subsequent post-inflammatory hyperpigmentation compared to traditional surface cryolipolysis techniques.

* * * * *